US007601141B2

(12) United States Patent
Dikeman et al.

(10) Patent No.: US 7,601,141 B2
(45) Date of Patent: Oct. 13, 2009

(54) PRESSURE ACTUATED FLOW CONTROL VALVE

(75) Inventors: W. Cary Dikeman, Leawood, KS (US); Thomas J. Solomon, Bellbrook, OH (US); Kerry L. Spiker, Xenia, OH (US)

(73) Assignee: Nexus Medical, LLC, Lenexa, KS (US)

( * ) Notice: Subject to any disclaimer, the term of this patent is extended or adjusted under 35 U.S.C. 154(b) by 217 days.

(21) Appl. No.: 10/304,833

(22) Filed: Nov. 26, 2002

(65) Prior Publication Data

US 2004/0102738 A1 May 27, 2004

(51) Int. Cl.
*A61M 5/00* (2006.01)

(52) U.S. Cl. ....................... 604/246; 604/247; 604/257; 604/19

(58) Field of Classification Search ................. 604/246, 604/167.01, 167.03, 167.04, 247, 256, 257, 604/19; 251/143, 149.1; 137/493.1, 846, 137/45, 515.7, 512.15; 473/611; 341/22, 341/173, 20; 340/10.2, 572.7, 572.1, 825.56, 340/825.69, 825.72; 345/168, 171, 172
See application file for complete search history.

(56) References Cited

U.S. PATENT DOCUMENTS 274,447 A * 3/1883 Kennish ..................... 251/143
1,923,501 A * 8/1933 Perry ......................... 473/611
2,524,764 A 10/1950 Burke
3,517,682 A * 6/1970 Smith ...................... 137/68.23
4,143,853 A * 3/1979 Abramson ............... 251/149.1
4,181,145 A 1/1980 Mitchell
4,341,239 A 7/1982 Atkinson
4,434,810 A * 3/1984 Atkinson .................... 137/493
4,995,863 A 2/1991 Nichols et al.

(Continued)

FOREIGN PATENT DOCUMENTS

EP 0416467 A2 3/1991

(Continued)

OTHER PUBLICATIONS

Printout from website for Vernay Laboratories, Inc. (www.vernay.com) depicting prior art bi-directional valve designated Part No. VL2959-101 (printed Feb. 2, 2007).

(Continued)

*Primary Examiner*—Kevin C. Sirmons
*Assistant Examiner*—Philip Gray
(74) *Attorney, Agent, or Firm*—Hovey Williams LLP

(57) ABSTRACT

A pressure actuated flow control valve for an infusion catheter permits gravity flow of a liquid through the catheter and into a patient while resisting back flow of blood from the patient and into the catheter. The valve has a hemispherical body with an outstanding circumferential flange and a normally closed, diametric slit. The slit is longer on the convex outer surface than on the concave inner surface. Dome thickness diminishes in the area adjacent the slit, reducing total apical deflection upon collapse of the slit toward the concave surface. An inner orthogonal rib biases the slit closed. Upon application of a predetermined pressure, the slit opens toward the concave surface to permit forward fluid flow. At lower pressures, the slit closes to check fluid flow. Greater reverse pressure is required to collapse the slit toward the concave surface to permit reverse fluid flow.

12 Claims, 6 Drawing Sheets

16 20 18 22 30 24 32 2 28 10 12 2 30 24 32 28 26 64 56 48 54 36 34 14 INTRAVASCULAR FLUID SOURCE 10 38 44 40 42

U.S. PATENT DOCUMENTS 5,147,313 A 9/1992 Dikeman
5,147,332 A 9/1992 Moorehead
5,160,325 A 11/1992 Nichols et al.
5,169,393 A 12/1992 Moorehead et al.
5,201,722 A 4/1993 Moorehead et al.
5,205,834 A 4/1993 Moorehead et al.
5,249,598 A * 10/1993 Schmidt .................. 137/493.1
5,251,873 A 10/1993 Atkinson et al.
5,295,657 A 3/1994 Atkinson
5,295,658 A 3/1994 Atkinson et al.
5,389,091 A 2/1995 Moorehead
5,402,982 A 4/1995 Atkinson et al.
5,409,471 A 4/1995 Atkinson et al.
5,431,202 A 7/1995 Dikeman et al.
5,501,426 A 3/1996 Atkinson et al.
5,533,708 A 7/1996 Atkinson et al.
5,843,044 A 12/1998 Moorehead
6,024,729 A 2/2000 Dehdashtian et al.
6,270,489 B1 8/2001 Wise et al.
6,364,867 B2 4/2002 Wise et al.
2002/0165492 A1 11/2002 Davey et al.

FOREIGN PATENT DOCUMENTS

FR 2707505 A1 1/1995

OTHER PUBLICATIONS

European Communication dated Sep. 10, 2007 from European Application No. 03029630.5, filed Dec. 22, 2003.
European Communication dated Jan. 29, 2007 from European Application No. 03029630.5, filed Dec. 22, 2003.
European Communication dated May 26, 2004 from European Application No. 03029630.5, filed Dec. 22, 2003.
European Communication dated Oct. 12, 2007 from European Application No. 07016563.4, filed Aug. 23, 2007.
English Translation of French Patent No. FR2707505, published Jan. 20, 1995, translation dated Nov. 2, 2007.
European Communication dated Oct. 16, 2007 from European Application No. 07016562.6, filed Sep. 28, 2007.

* cited by examiner

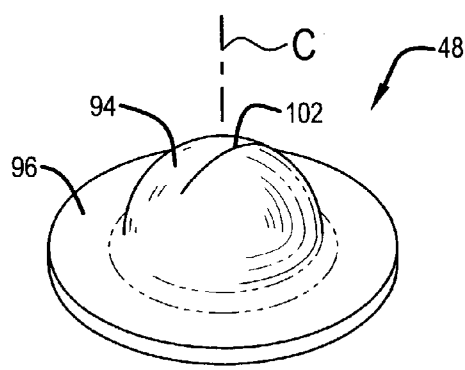
Fig. 3
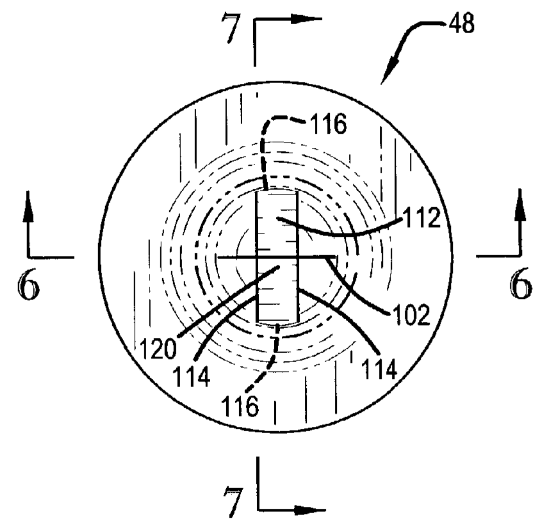
Fig. 4
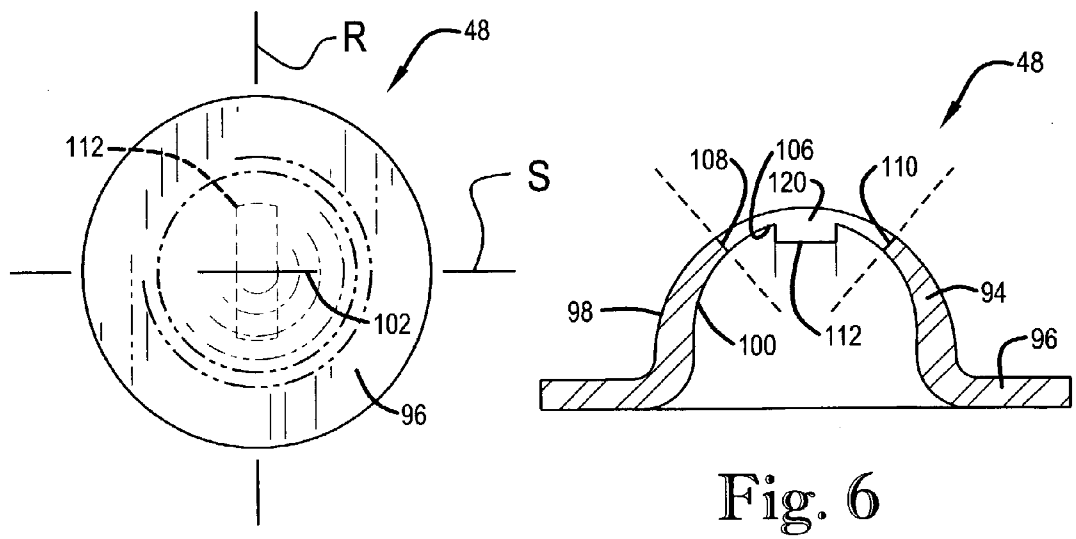
Fig. 6
Fig. 5

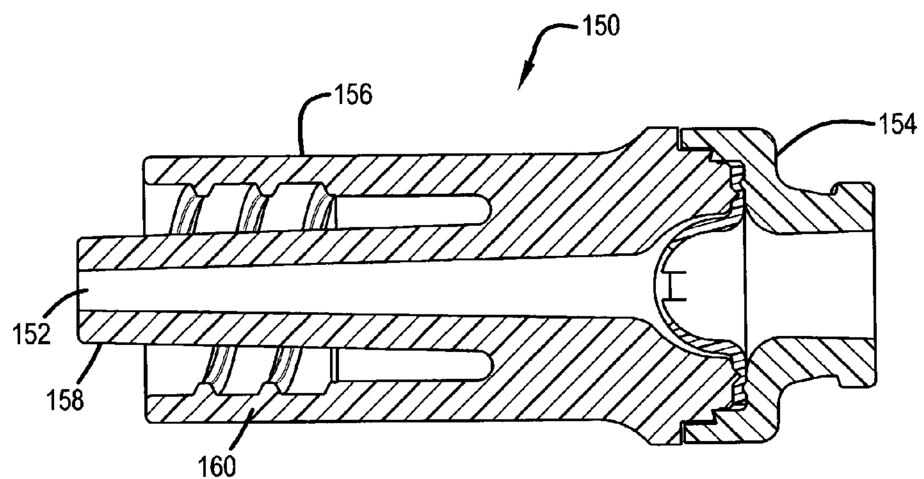
Fig. 10
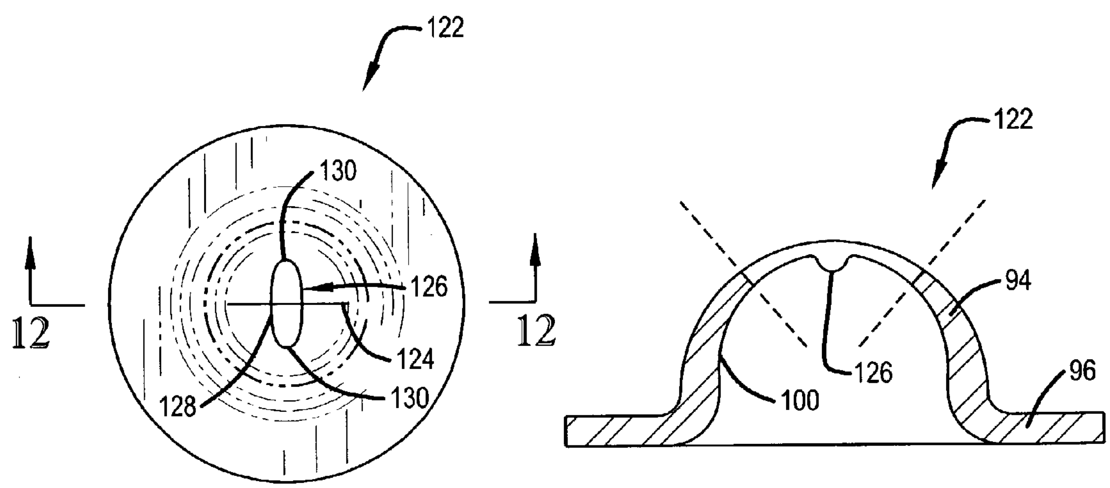
Fig. 11
Fig. 12

PRESSURE ACTUATED FLOW CONTROL VALVE

BACKGROUND OF THE INVENTION

The present invention is broadly concerned with a control valve for a medical fluid infusion device. More particularly, it is concerned with a positive pressure actuated flow control valve that permits flow of a liquid from a reservoir, through a cannula and into a patient, while resisting reflux.

Medical infusion therapy employs peripheral and central intravascular devices such as venous and arterial catheters as well as peripherally inserted central venous catheters to deliver fluids, blood products, and pharmaceuticals, including antibiotics and biologics as well as parenteral nutrition. Intravascular devices may also be coupled with pressure monitoring systems.

Regardless of the location of the insertion site of the catheter or the placement of its terminus, intravascular devices, and central venous catheters (CVCs) in particular, are subject to retrograde blood flow into the catheter lumen whenever the pressure in the patient's vascular system exceeds resistance at the supply end of the catheter. This may occur, for example, when fluid pressure drops because a gravity supply source is empty, when an injection port is opened by removal of a syringe, or when a stopcock is opened.

Retrograde blood flow is known to contribute to complications such as catheter-related septicemia, venous thrombosis, superior vena cava syndrome, pulmonary embolism and phlebitis. Thrombus formation may cause partial or complete occlusion of the catheter. Partial occlusion results in impaired sampling and fluid administration. Complete occlusion causes the catheter to lose patency, necessitating removal and replacement, so-called "unscheduled restarts".

Catheter reflux-induced thrombosis is not merely a mechanical complication, since it appears to be a major contributor to catheter related bloodstream infections associated with the use of long term catheters. Such infections are associated with increased morbidity and mortality as well as increased health care costs associated with extended hospitalization.

Attempts have been made to develop improved intravascular devices in order to address the mechanical and infectious complications previously described. Peripherally inserted central venous catheters (PICCs) are known to reduce the incidence of thrombosis and phlebitis as well as commonly reported central catheter-related infections. However, PICC devices are not suitable for all applications, particularly where the solution to be administered has high osmolarity or may be a pH irritant. And patients with PICC infusion still experience thrombus formation and phlebitis at statistically significant levels.

Guidewire assisted exchange has also been employed to achieve a lower rate of mechanical complications following insertion of replacement catheters. However, patients may experience bleeding, hydrothorax and subsequent catheter related infections.

In-line filters have also been employed to reduce infusion-related phlebitis. However, they have not been found to prevent intravascular device-related infections. And use of such filters is not regarded as mechanically favorable, since solution filtration may be accomplished more efficiently prior to infusion and the filters themselves are subject to blockage.

Impregnated catheters and needle-free devices have also been employed. Although they have not yet been thoroughly evaluated, antimicrobial coated or impregnated catheters appear to be more effective for central venous use than for peripheral use. There are concerns, however, that they may foster development of resistant bloodstream pathogens. Needle-free infusion systems also have not yet been fully studied, although one investigation has shown survival of skin flora in needleless infusion systems.

There have also been attempts to develop methods of using conventional intravascular devices in order to prevent catheter-related thrombus formation and to maintain catheter patency. Turbulent positive pressure flushing with anticoagulant heparin solution, use of thrombolytic agents such as urokinase, streptokinase and t-Pa, and prophylactic warfarin administration have all been employed.

However, some in vitro studies have suggested that heparin flush solutions may serve to enhance growth of Coagulase-negative staphylococci (CoNS). The United States Public Health Service, Centers for Disease Control and Prevention (CDC) has cited CoNS as "the primary pathogen causing catheter-related infections". It has recommended clinical trials to evaluate the practice of flushing with anticoagulant solutions to prevent catheter-related infections. The CDC has also cited an association between use of low dose heparin and thrombocytopenia and thromboembolic and hemorrhagic complications.

All of the preventive methods that are currently available appear to contribute in some manner to general health care delivery problems, such as delay, increased requirements for nursing care, pharmaceutical and supply costs, increased patient risk and discomfort.

Accordingly, there is a need for an improved intravascular device that will resist retrograde blood flow and thereby reduce rates of thrombus formation, catheter-related blood stream infection, and unscheduled restarts and thereby extend catheter indwelling times.

SUMMARY OF THE INVENTION

The present invention is directed to a pressure actuated flow control valve for an infusion catheter which permits gravity flow of a liquid through the catheter and into a patient while resisting back flow of blood from the patient and into the catheter. The valve includes a hemispherical dome-shaped body having concave inner and convex outer surfaces. A normally closed, slit communicates between the surfaces. The slit is configured so that it is longer on the convex outer surface than on the concave inner surface. The cross-sectional thickness of the dome diminishes in the area adjacent the slit, reducing total apical deflection upon collapse of the slit toward the concave surface. The dome inner surface includes an orthogonal rib that biases the wall of the dome adjacent the slit to a closed position. Upon application of a predetermined pressure, the slit opens toward the convex surface for facilitating fluid flow in the intended direction. At lower pressures, the slit resumes a closed position to check fluid flow. Relatively greater reverse pressure is required to collapse the slit toward the concave surface to permit reverse fluid flow. The valve includes an outstanding circumferential flange for engagement within a housing.

Objects and advantages of this invention will become apparent from the following description taken in conjunction with the accompanying drawings wherein are set forth, by way of illustration and example, certain embodiments of this invention.

BRIEF DESCRIPTION OF THE DRAWINGS

FIG. 3 is a front perspective view of the valve depicted in FIG. 1.

FIG. 4 is an enlarged bottom plan view of the valve depicted in FIG. 1.

FIG. 5 is an enlarged top plan view of the valve depicted in FIG. 1, showing the rib in phantom.

FIG. 6 is a further enlarged sectional view taken along line 6-6 of FIG. 4 and shows details of the valve slit.

FIG. 10 is an enlarged sectional view of a valve assembly incorporating an alternate threaded Luer housing.

FIG. 11 is an enlarged bottom plan view of an alternate valve having a cylindrical rib configuration.

FIG. 12 is an enlarged sectional view taken along line 12-12 of FIG. 11 and shows details of the valve slit.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words “distally” and “proximally” will refer to directions respectively toward and away from a patient.

Figure 1:
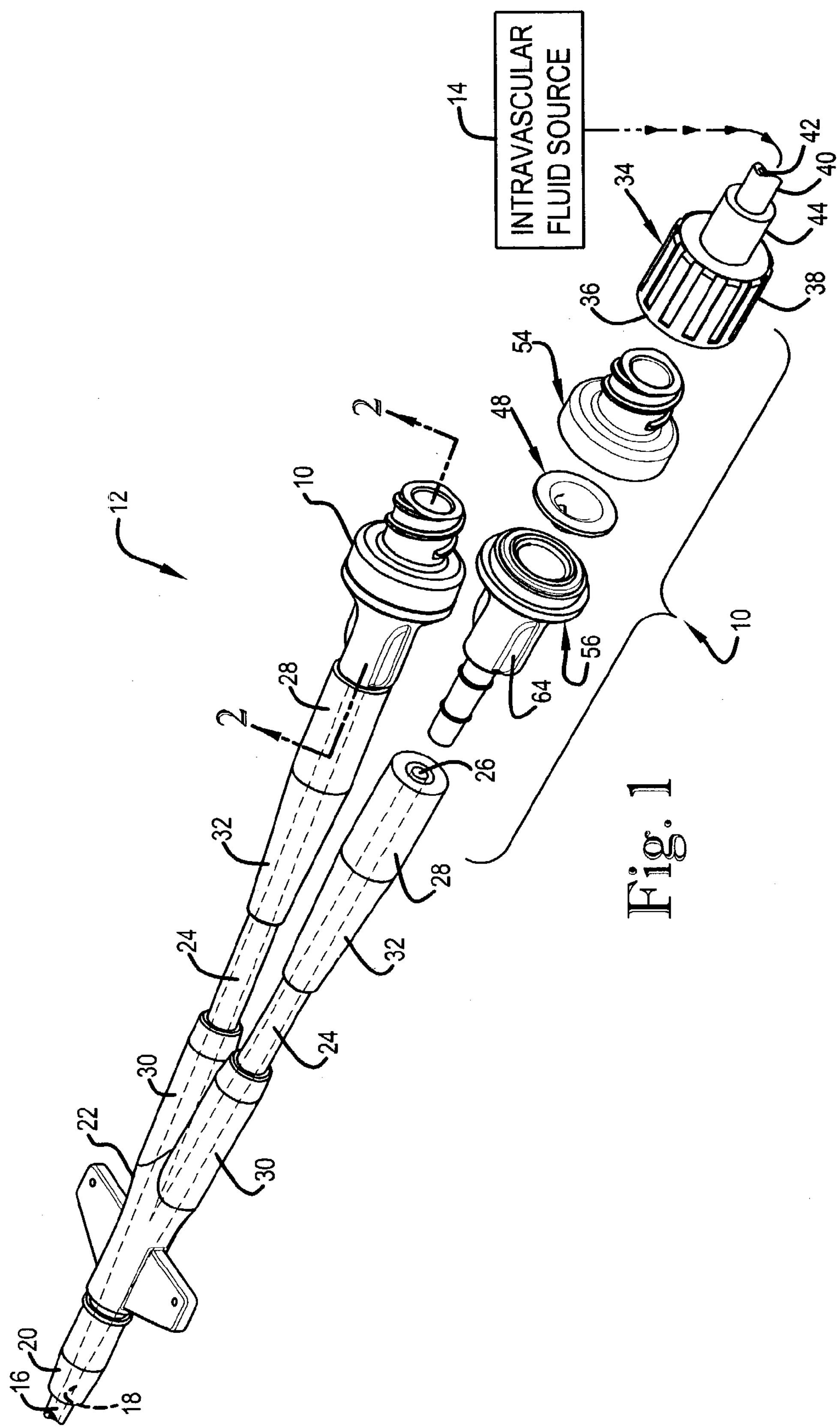
FIG. 1 is a combination diagrammatic and perspective, partially exploded view of a flow control valve assembly in accordance with the invention, installed in a medical fluid infusion system.
Figure 2:
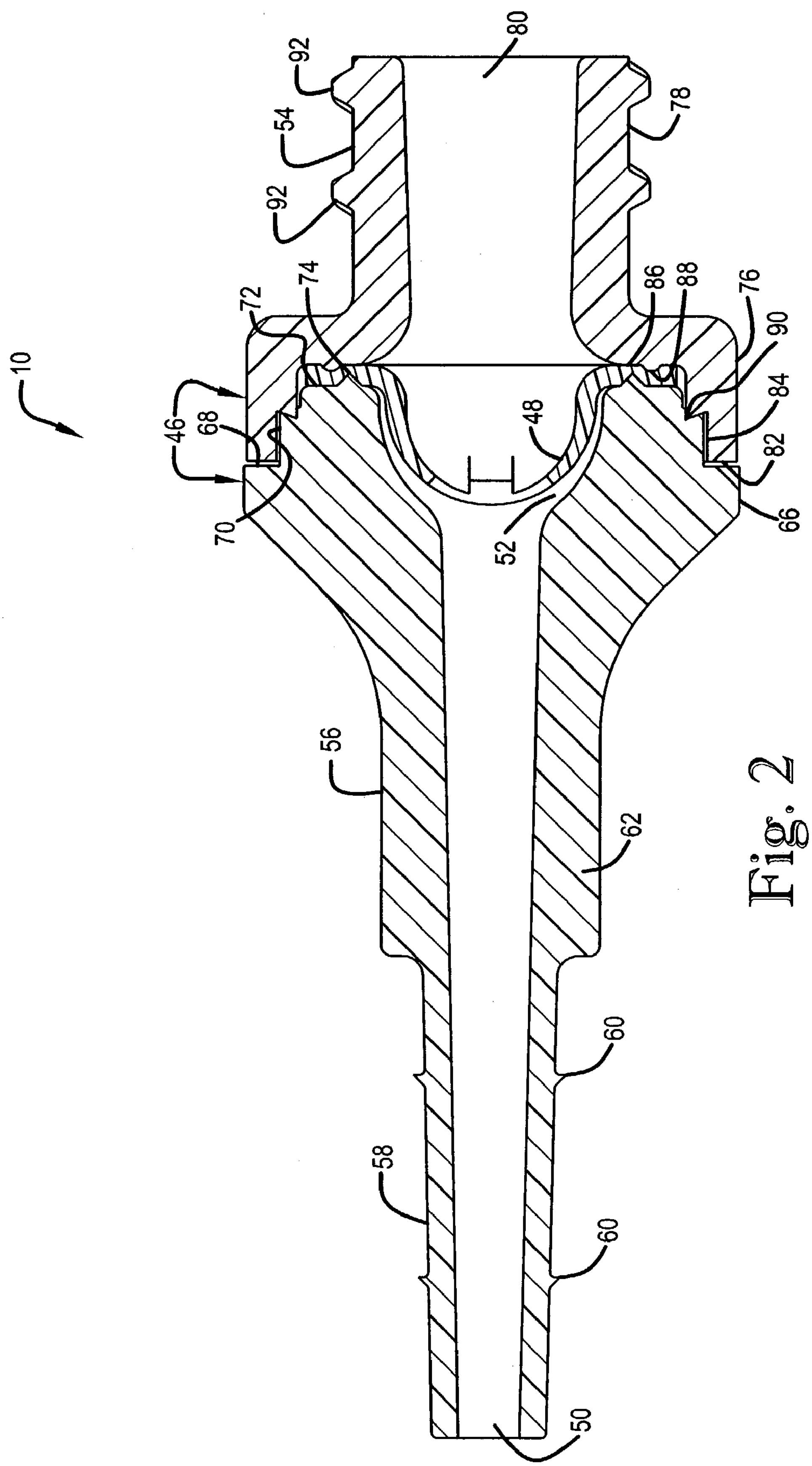
FIG. 2 is an enlarged sectional view taken along line 2-2 of FIG. 1 and shows details of the housing construction.

Referring now to the drawings, a pressure actuated flow control valve assembly in accordance with the invention is generally indicated by the reference numeral 10 and is depicted in FIGS. 1 and 2. FIG. 1 illustrates exemplary use of the valve assembly 10 installed in-line between an intravascular device 12 such as an intravenous (IV) fluid delivery catheter set and an intravascular fluid source 14, such as an IV fluid reservoir. Those skilled in the art will appreciate that the pressure actuated valve assembly 10 can also be used in conjunction with a variety of other medical fluid delivery devices, such as an arterial catheter and associated chemotherapy fluid reservoir and/or pressure monitoring device, or a gastrostomy tube set having a corresponding fluid reservoir.

The intravascular device 12 includes an elongate, flexible catheter 16 having an outer surface and an inner surface defining a lumen or fluid passageway 18. A distal end of the catheter 16 is adapted for insertion into a vein of a patient. The outer surface of the proximal end of the catheter 16 is overmolded by a compression strain relief cuff 20 and is coupled with a Y-connector 22, which serves as a manifold for coupling a pair of connector tubes 24 in fluidic communication with the single catheter 16. Each connector tube 24 has an outer surface and an inner surface defining a lumen 26, and proximal and distal end portions 28 and 30 respectively. The proximal end portions 28 are each overmolded by a compression strain relief cuff 32. The Y-connector 22 receives the distal end portions 30. While FIG. 1 depicts an intravascular device 12 having two connector tubes 24, it is foreseen that any operable number of such tubes may be employed, including a single tube. In addition, while FIG. 1 depicts only the distal end of the catheter 16 as indwelling, the entire intravascular device 12 may be constructed for indwelling installation and use.

As more fully described herein, each connector tube proximal end portion 28 is coupled with a valve assembly 10, which in turn is coupled with a connector 34. The connector 34 has a generally cylindrical overall shape and is hollow and open at one end to receive the valve assembly 10. The connector 34 includes a threaded interior surface 36 and an exterior surface 38 that is swaged or flanged to facilitate gripping. One end of the connector 34 is axially apertured to permit coupling with a supply tube 40 having an outer surface and an inner surface defining a fluid passageway or lumen 42. The outer surface of the supply tube 40 adjacent the connector 34 is equipped with a molded fitment 44 to accommodate tubing attachment. The proximal end of the supply tube 40 is coupled with the fluid reservoir 14 so that the lumen 42 is in fluidic communication with the reservoir 14.

Although not shown in FIG. 1, the connector 34 may also be equipped with a stopcock or a plurality of infusion ports with plugs for receiving a syringe and/or needle. A pump may be installed in line with the supply tube 40, which may also be equipped with clamps (neither is shown).

The catheter 16, connector tubes 24 and supply tube 40 are flexible and pliant to facilitate placement, usage, and to minimize both mechanical insult to the blood vessels and patient discomfort during long-term use. They may be constructed of any suitable medical grade material, such as, for example, polyethylene, polyvinyl chloride, Teflon, silicone elastomer or polyurethane or mixtures thereof. The material may be coated or impregnated with an antimicrobial or antiseptic composition to reduce bacterial adherence and biofilm formation. The catheter 16 may also be constructed of a radiopaque material in order to facilitate imaging for locating any breaks and/or separated sections.

The strain relief cuffs 20 and 32 and fitment 44 are constructed of an elastomeric medical grade synthetic resin material. The connector 34 may be constructed of a medical grade rigid or semirigid synthetic resinous material suitable for supporting an operable threaded connection, such as, for example, polyvinyl chloride or polycarbonate.

As best shown in FIGS. 1 and 2, the valve assembly 10 broadly includes a housing 46 supporting a valve member 48. The housing 46 has an elongate, stepped external configuration surrounding an internal fluid passageway or lumen 50. The lumen 50 has an enlarged diameter adjacent the proximal end to form a hemispherical cavity 52 sized for receiving the dome-shaped valve 48. The housing 46 includes a hub portion 54, which is shown positioned for installation in a proximal orientation and a body portion 56 shown in a distal orientation. The housing 46 is formed of a suitable medical grade synthetic resin, such as for example, a polycarbonate.

The body 56 includes a tapered nipple 58 sized for reception within the lumen 26 of a connector tube 24. The nipple 58 includes a plurality of spaced, radially expanded annular barbs 60. While FIG. 1 depicts two barbs 60 evenly spaced along the nipple 58, it is foreseen that any number of barbs 60 may be included with any suitable degree of radial expansion and in any spaced configuration.

The proximal end of the nipple 58 is radially expanded to form a midportion or barrel 62, having a pair of opposed axial flanges or finger tabs 64 to facilitate manual rotation of the valve assembly 10. The barrel 62 is radially expanded at the proximal end to form an annular seat 66 for receiving the hub 54. The seat 66 includes a series of concentric steps 68 perpendicular to the axis of the lumen 50, each step 68 presenting a concentric side wall 70, which is coaxial with the lumen 50. The proximal step 68 serves as a valve seat 72. The surface of the valve seat 72 includes a raised annular ring or stake 74, having an angular or pointed, proximal surface adapted for gripping engagement of a valve 48.

The hub 54 has a hollow, stepped cylindrical configuration, including a distal skirt portion 76 and a proximal neck 78 with a central lumen 80. The inner surface of the skirt includes a series of concentric steps 82, each including a concentric side wall 84 for mating engagement with respective corresponding steps 68 and side walls 72 of the body portion 56. The proximal step serves as a valve seat 86. The surface of the valve seat 86 includes a raised annular ring 88, for gripping engagement of a valve 48. One of the steps 82 subtends an angle of less than 90° to form an energy director 90. The neck 78 includes a series of female Luer lock threads, 92 designed for mating engagement with corresponding standard male IV Luer threads in the connector 34. Alternately, a conventional threaded or bayonet-type fitting may be substituted in the neck 78 and connector 34 for the Luer fittings shown and described.

As best shown in FIGS. 3-9, the valve member 48 includes a dome portion 94 coupled with an outstanding radial flange or lip portion 96. It is also foreseen that the flange 96 may be of lesser radial extent or omitted entirely. The valve 48 has outer and inner surfaces 98 and 100 respectively and includes a circumferential slit 102 centered on the dome 94. The slit 102 extends across the fluid flow path for providing fluid communication through the valve 48 when it is in an open position. As best shown in FIGS. 3 and 5, the slit 102 is bisected by a central axis C, is coplanar with a slit axis S, and is crossed by a rib axis R perpendicular to axis S. As shown in FIG. 6, the slit 102 has outer and inner margins 104 and 106 and a pair of ends 108 and 110. Because the outer margin 104 is longer than the inner margin 106, the ends 108 and 110 subtend an angle.

Figure 7:
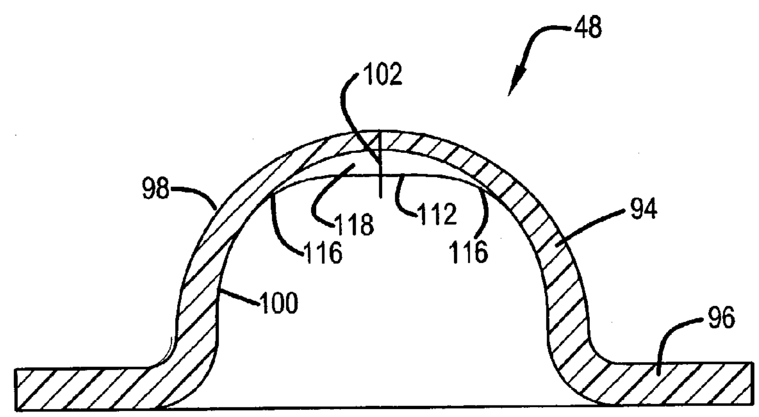
FIG. 7 is a still further enlarged sectional view taken along line 7-7 of FIG. 4 and shows details of the rib.

As illustrated in FIGS. 6 and 7, the outer surface 98 of the valve dome 94 has the symmetrical configuration of a hemisphere. It is also foreseen that the dome 94 may be configured as a spherical cap or chordal segment (the region of a sphere that lies above a chordal plane that does not pass through the center of the sphere) which may be either greater or less than one-half of a sphere. The valve dome 94 need not be strictly hemispherical or partially spherical; however it is preferred that it be at least dome-like or cap-like. The outer and inner surfaces 98 and 100 of the valve dome 94 are not perfectly concentric. The inner surface 100 of the valve dome 94 is depicted as having a generally hemispherical configuration, with a slightly increased curvature as it approaches the axis C. As a result, the dome 94 has a variable wall thickness, which diminishes as it approaches an apex region of the dome 94 at the axis C.

The inner surface 100 of the valve dome 94 is shown in FIGS. 4 and 6-7 and in FIG. 5 in phantom to include an elongate rib 112. The rib 112 extends generally circumferentially inwardly in the direction of axis R, perpendicular to and centered on the slit 102, and serves to bias the slit 102 to the closed position depicted in FIG. 3. The rib 112 is of approximately rectangular overall configuration, including a pair of spaced, parallel side surfaces or sides 114 and a pair of ends 116 convergent with the inner surface 100 of the valve dome 94.

As shown in FIGS. 6 and 7, the rib 112 has a depth 118 which diminishes as the ends 116 are approached. The rib 112 may be constructed so that the depth 118 also diminishes as the sides 114 are approached. The rib 112 is bisected by the slit 102 at a center portion 120 of the rib. Thus, the wall thickness of the dome thins as it approaches the geometric center of the slit 102, and is reinforced at the center along axis R by the depth of the rib 112. It is foreseen that, rather than bisecting the rib 112, the slit 102 may intersect the rib 112 eccentrically or asymmetrically, or that the slit 102 may be coextensive with the rib 112. It is also foreseen that the ends of the rib 116 could be truncated (not shown) so that the depth 118 does not diminish as the ends 116 are approached, or that the ends 116 could be constructed so that the depth 118 increases as the ends are approached.

FIGS. 11 and 12 depict a valve 122 having an alternate rib construction. The structure of the valve 122 is substantially identical to that previously described, and the numbering and description of like elements and axes is hereby adopted and will not be reiterated. The valve 122 includes a circumferential slit 124 centered on the dome 94. The inner surface 100 of the dome 94 includes a rib 126 having an approximately hemi-cylindrical overall configuration, including a curvate surface 128 and a pair of ends 130 convergent with the inner surface 100 of the valve dome 94. As previously described, the rib depth diminishes as the ends 130 are approached.

Figure 13:
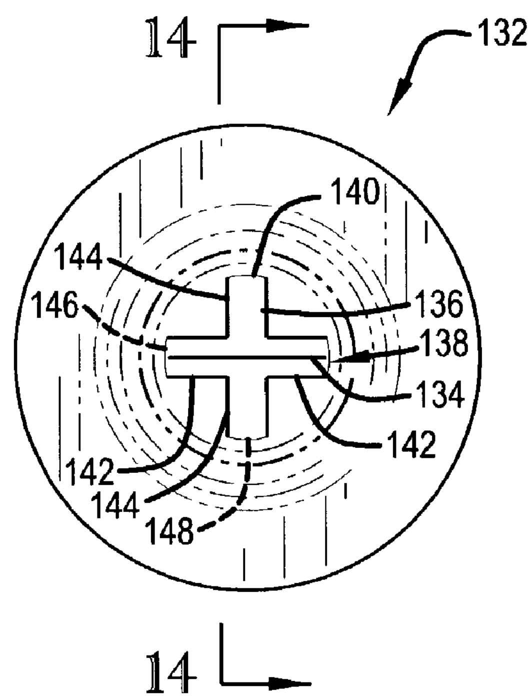
FIG. 13 is an enlarged bottom plan view of a second alternate valve having a cruciform rib configuration.
Figure 14:
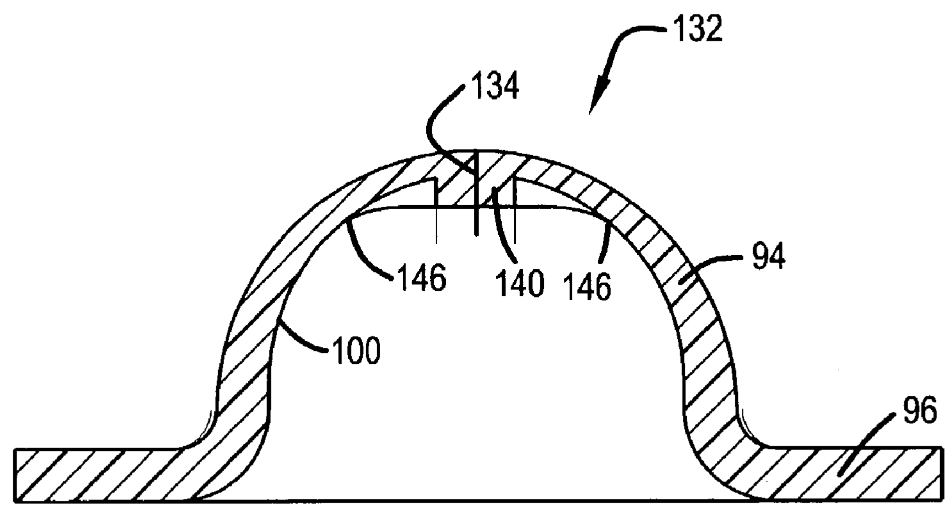
FIG. 14 is an enlarged sectional view taken along line 14-14 of FIG. 13 and showing details of the rib.

FIGS. 13 and 14 depict a valve 132 having a second alternate rib construction. The structure of the valve 132 is also substantially identical to that previously described, and the numbering and description of like elements and axes is also adopted and will not be reiterated. The valve 132 includes a circumferential slit 134, also centered on the dome 94. The inner surface 100 of the valve dome 94 includes a rib 136 having an approximately X-shaped or cruciform overall configuration. The rib 136 has a first leg 138 and a second leg 140, each of approximately rectangular overall configuration. Each of the legs 138 and 140 include a pair of sides 142 and 144, and a pair of ends 146 and 148 respectively. The first leg 138 is coextensive with the slit 134, whereas the second leg 140 is orthogonal to the slit 134. The leg ends 146 and 148 are convergent with the inner surface 100 of the valve dome 94. As previously described, the rib depth diminishes as the ends 146 and 148 are approached. Those skilled in the art will appreciate that, in addition to the rib configurations previously described, the rib may be of oblong, elliptical, quadrilateral, star-shaped, curvate, compound curvate, circular, curvilinear or any other suitable configuration.

The valve dome 94, lip 96 and ribs 112, 126 and 136 are of unitary construction and are formed of a resilient medical grade elastomeric material such as a silicone elastomer. The characteristics of the material used to construct the valve 48 and housing 46, the dimensions of the valve dome 94, flange 96, ribs 112, 126 and 136 and slit 102, 124 or 134 the wall thickness of the valve 48 as well as the magnitude of thinning of the wall as it approaches the top of the dome 94 and location of the slit 102, 124 or 134 (whether centered on the dome or eccentric) are variables which collectively determine both the magnitude and difference between individual pressure differentials $P_1$ and $P_2$ under which the slit 102, 124 or 134 flexes in forward and reverse fluid-enabling manner.

The valve assembly 10 may be constructed by aligning the valve member 48 or 122 or 132 on the body portion 56 of the housing 46 so that the outer surface 98 of the valve flange 96 engages the body valve seat 72 and projecting stake 74, and is received within cavity 52.

The hub 54 is installed over the body 56 with the body and hub steps 68 and 82 in mating engagement and the hub valve seat 86 and projecting ring 88 overlying the valve flange 96. The hub 54 and body 56 are then subject to ultrasonic welding under pressure to form a hermetic seal. The energy director 90 serves to direct the ultrasonic melt, so that the surfaces of the mated steps 68 and 82 fuse and the valve flange 96 is captured between the stake 74 and the ring 88 in a generally S-shaped cross sectional configuration as depicted in FIG. 2. In this manner, the valve 48 or 122 or 132 is secured in place against dislodgement by fluid pressure or force exerted by any object which might be inserted into the housing lumen 50. Alternatively, the hub 54 and body 56 may be secured together by an adhesive composition, by a strictly mechanical junction, or by other arrangements.

The valve assembly may be installed in an intravascular device 12 by grasping the housing 47 and using the finger tabs 64 to rotatingly introduce the nipple 58 into the lumen 26 at the proximal end portion 28 of a connector tube 24 until all of the barbs 60 are received within the lumen 26. The barbs 60 serve to frictionally engage the inner surface of the connector tube lumen 26 in a force fit. It is foreseen that, where a single IV line is to be employed, a connector tube 24 may be unnecessary so that the housing 46 may be introduced directly into the catheter lumen 18 at the proximal end of a catheter 16. A connector 34 is aligned over the neck 78 and rotated until the threaded interior surface 36 tightly engages the threads 92 of the neck 78. More than one valve assembly 10 may be installed in-line in an intravascular device 12.

In use, the catheter 16 is inserted into a blood vessel of a patient, so that the catheter lumen 18 is in fluidic communication with the patient's blood. If the catheter 16 is to be centrally placed, it is then threaded into a large central vein where it may remain indwelling for a prolonged period of time.

An intravascular fluid source or reservoir 14 is coupled with the supply tube 40 so that the supply tube lumen 42 is in fluidic communication with the reservoir. Gravity fluid flow is initiated from the fluid source 14 by any conventional means, such as by opening a stopcock or removing a clamp. Fluid flow may also be initiated by actuating a pump. Fluid from the reservoir 14 travels in a flow path through the supply tube 40 into the housing lumen 50 and through the valve 48 or 122 or 132 until it contacts the inner surface 100 of the dome.

Figure 8:
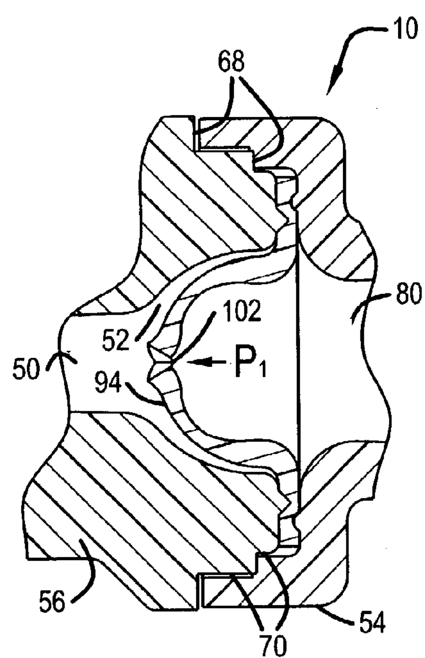
FIG. 8 is a fragmentary sectional view similar to the view shown in FIG. 2 at a reduced scale, showing the valve in an open, forward fluid flow enabling position.

As shown in FIG. 8, when the forward fluid flow exerts or exceeds a predetermined fluid pressure differential $P_1$ or cracking pressure against the dome inner surface 100, the slit 102 flexes distally to an open, forward flow-enabling position. In valves 122 and 132, similar pressure conditions cause similar flexion of the respective slits 124 and 134. The axial thinning of the dome 94, the shorter length of the slit inner margin 106 with respect to the slit outer margin 104, and the angle subtended by the ends of the slit 108 and 110 all cooperate to facilitate flexing of the slit 102 or 124 or 134 at a relatively low pressure differential, such as is provided by the force of gravity on an elevated fluid reservoir.

The slit 102 or 124 or 134 remains in an open position to permit the flow of fluid in a forward direction as long as the pressure differential $P_1$ is maintained against the dome inner surface 100. When the fluid supply in the fluid reservoir 14 is exhausted, the pressure differential against the dome inner surface 100 falls below the cracking pressure $P_1$, and the rib 112, or 122 or 128 serves to bias the slit 102 or 124 or 134 back into a closed, flow-blocking position, depicted in FIG. 7. The rib 112, or 122 or 128 also biases the closed slit margins 104 and 106 into sealing alignment, so that there is no overlap which might permit leakage through the valve. The pressure differential $P_1$ is preselected by design so that the slit 102 or 124 or 134 closes while a fluid head remains in the supply tube 40, so that air does not enter the valve 48 or 122 or 132.

Figure 9:
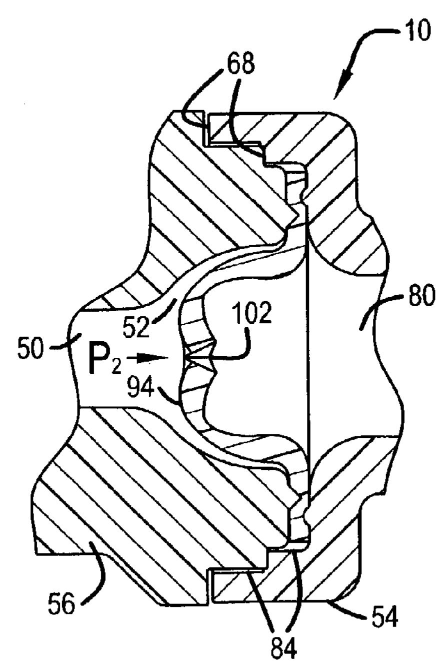
FIG. 9 is similar to the view depicted in FIG. 8, showing the valve in a collapsed, reverse fluid flow enabling position.

At times, it may be necessary to permit reverse fluid flow, for example to withdraw a blood sample. In such instances, a syringe may be inserted into the hub 54 and the plunger withdrawn to create a negative pressure. As shown in FIG. 9, when a predetermined fluid pressure differential $P_2$, or collapsing pressure, is exerted or exceeded against the dome outer surface 98, the slit 102 or 124 or 134 flexes proximally to an open, reverse flow-enabling position. Flexing of the slit is accompanied by proximal collapse of a portion of the dome 94. Because of the axial thinning of the dome 94 in the region of the slit once the pressure differential $P_2$ is reached, only a limited portion of the dome flexes proximally, and the entire dome 94 does not invert into the hub lumen 80. In this manner, the volume of fluid displace back in to the housing lumen 50 is minimized when the pressure falls below $P_2$ and the rib 112 or 122 or 128 biases the slit 102 or 124 or 134 back into a closed, fluid flow blocking position depicted in FIG. 7. Advantageously, the combination of the hemispherical shape of the dome 94, the angular ends of the slit 102, the anterior thinning of the dome 94 in the region of the slit 102 or 124 or 134, and the rib 112 or 122 or 128 combine to provide a valve 48 having a relatively low cracking pressure $P_1$, a relatively high reflux pressure $P_2$ and minimal fluid displacement following reverse fluid flow. This combination of features permits forward fluid flow by gravity from a reservoir and into a patient, while inhibiting thrombus promoting fluid backflow and minimizing reflux volume.

The structure of a an alternate valve assembly housing is illustrated in FIG. 10 and is generally indicated by the reference numeral 150. The housing 150 has an elongate, generally cylindrical external configuration surrounding a fluid passageway or lumen 152, which widens proximally for receiving the dome-shaped valve member 48 previously described. The housing 150 includes a hub portion 154 and a body portion 156.

The distal portion of the body 156 is configured as a standard Luer connector, including a standard Luer taper 158 and standard male luer lock threaded overmantle 160 or internally threaded collar. The proximal portion of the body 156 and distal portion of the hub 154 are matingly stepped as previously described with respect to the body 56 and hub 54. The proximal portion of the hub 154 is configured with a truncated, Luer threaded top 162.

In use, the male Luer body 156 may be rotatingly coupled with any standard female Luer connection, while the female Luer hub 154 may be coupled with any standard male Luer connection in order to install the valve assembly housing 150 in-line between an intravascular fluid source and an indwelling catheter 16. The operation of the valve member 48 within the housing 150 is substantially the same as previously described with respect to the valve member 48 within the housing 46.

It is to be understood that while certain forms of the present invention have been illustrated and described herein, it is not to be limited to the specific forms or arrangement of parts described and shown.

Having thus described the invention, the following is claimed as new and desired to be secured by Letters Patent:

1. A pressure-actuated valve component for use in IV therapy to control fluid flow through a catheter in opposite infusion and aspiration directions, said valve component comprising:

a housing including spaced apart intravenous fluid ports and a tapered male fitting that defines one of the ports and is operable to be fluidly coupled to the catheter, with a fluid passageway extending between the ports to present a passageway axis; and a valve body being disposed within the fluid passageway and including a flexible dome-shaped wall that presents a convex surface and an opposite concave surface, with the convex surface facing the infusion direction and the concave surface facing the aspiration direction, said dome-shaped wall including a normally closed slit extending between the surfaces and intersecting the passageway axis, said dome-shaped wall flexing to open the slit in response to an infusion fluid pressure differential across the wall, wherein the pressure against the concave surface is greater than the pressure against the convex surface, said dome-shaped wall flexing to open the slit in response to an aspiration fluid pressure differential across the wall, wherein the pressure against the convex surface is greater than the pressure against the concave surface, said valve body including a rib projecting from the concave surface in an orthogonally extending relationship to the slit, said slit intersecting said convex surface to form a convex arc having a convex arc length, said slit intersecting said concave surface to form a concave arc having a concave arc length, said convex arc length being greater than said concave arc length, with the slit presenting termination ends that are each at an oblique angle relative to the passageway axis, said slit intersecting the rib and extending along the dome-shaped wall radially outwardly from the rib relative to the axis so that the slit termination ends are spaced from the rib.

2. The pressure-actuated valve component as claimed in claim 1, said wall having an outstanding circumferential flange secured to the housing.

3. The pressure-actuated valve component as claimed in claim 1, said convex and concave ares subtending a common angle.

4. The pressure-actuated valve component as claimed in claim 1, said slit and rib being located generally at the apex.

5. The pressure-actuated valve component as claimed in claim 1, said dome-shaped wall being flexed to open the slit while the infusion fluid pressure differential exceeds a threshold infusion pressure, said dome-shaped wall being flexed to open the slit while the aspiration fluid pressure differential exceeds a threshold aspiration pressure, said threshold infusion pressure being less than the threshold aspiration pressure.

6. The pressure-actuated valve component as claimed in claim 1, said dome-shaped wall being flexed to open the slit while the aspiration fluid pressure differential exceeds a threshold aspiration pressure, said dome-shaped wall being only partly inverted when the aspiration fluid pressure differential exceeds the threshold aspiration pressure.

7. The pressure-actuated valve component as claimed in claim 1, said dome-shaped wall having a thickness that diminishes apically.

8. The pressure-actuated valve component as claimed in claim 7, said dome-shaped wall having a thickness that diminishes apically.

9. The pressure-actuated valve component as claimed in claim 1, said dome-shaped wall being hemispherical in shape.

10. The pressure-actuated valve component as claimed in claim 9, said hemispherical shape being symmetrical about the passageway axis.

11. The pressure-actuated valve component as claimed in claim 9, said dome-shaped wall having a thickness that diminishes apically.

12. The pressure-actuated valve component as claimed in claim 11, said wall thickness diminishing continuously to the apex.

* * * * *